(12) United States Patent
Nazarian et al.

(10) Patent No.: US 10,220,119 B2
(45) Date of Patent: Mar. 5, 2019

(54) ACTIVATION OF ANTIMICROBIAL AGENTS

(71) Applicant: Beth Israel Deaconess Medical Center, Inc., Boston, MA (US)

(72) Inventors: Ara Nazarian, Watertown, MA (US); Edward Kenneth Rodriguez, Medfield, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 317 days.

(21) Appl. No.: 15/129,239

(22) PCT Filed: Mar. 25, 2015

(86) PCT No.: PCT/US2015/022574
§ 371 (c)(1),
(2) Date: Sep. 26, 2016

(87) PCT Pub. No.: WO2015/148726
PCT Pub. Date: Oct. 1, 2015

(65) Prior Publication Data
US 2017/0173218 A1    Jun. 22, 2017

Related U.S. Application Data

(60) Provisional application No. 61/970,783, filed on Mar. 26, 2014, provisional application No. 61/979,866, filed on Apr. 15, 2014.

(51) Int. Cl.
*A61L 27/54* (2006.01)
*A61L 31/16* (2006.01)
(Continued)

(52) U.S. Cl.
CPC .............. *A61L 27/54* (2013.01); *A61L 2/24* (2013.01); *A61L 27/047* (2013.01); *A61L 31/16* (2013.01);
(Continued)

(58) Field of Classification Search
CPC .......... A61L 27/54; A61L 2/24; A61L 27/047; A61L 31/16; A61L 2300/10; A61N 1/325;
(Continued)

(56) References Cited

U.S. PATENT DOCUMENTS 6,032,677 A    3/2000 Blechman et al.
2005/0107847 A1    5/2005 Gruber et al.
(Continued)

OTHER PUBLICATIONS

International Search Report and Written Opinion for Application No. PCT/US2015/022574 dated Jul. 2, 2015.
(Continued)

*Primary Examiner* — Manuel Mendez
(74) *Attorney, Agent, or Firm* — Wolf, Greenfield & Sacks, P.C.

(57) ABSTRACT

Post-operative infection in joint prostheses is a problem due to adverse consequences such as surgical debridement or implant removal. Embodiments create a coating that can be powered to release microbicidal agents to both ensure the prevention of infections, and avoid the development of antibiotic resistance. Silver ions have been well established for antimicrobial characteristics, and thus make an advantageous implant coating. Reverse electrolysis allows the ions to be released for a sustained period of time, and then collected back onto to the implant to avoid silver poisoning. A wireless reverse electrolysis system releases a sufficient amount of silver ions to break down biofilm surrounding a joint implant. By applying a modulated current waveform that has a net negative value to a conducting copper strip, the mirror current induced on the silver coating surface has a net positive flow, allowing ions to be released into surrounding tissue. Using this method, an average silver concentration of 32 ppb is created in surrounding medium after 12 hours, sufficient to eradicate bacteria directly around the silver. The ability to wirelessly induce electrolysis of silver ions to kill
(Continued)

Plot for direct electrolysis experiments in both NaCl solution and purified water solution, both with an applied current of 20 μA. The triangles show the NaCl solution results, which remain at 0ppb at different time periods, while the diamonds show the results in purified water, each for experiments that lasted different lengths of time. As seen in the plot, in purified water, an exponential best fit curve was applied and showed that the concentration of silver ions increases exponentially as time increases, with an R2 value of 0.911.

a significant quantity of bacteria can be used in surgical procedures to avoid post-operative infection in joint prostheses.

35 Claims, 13 Drawing Sheets

(51) Int. Cl.
    *A61N 1/32*     (2006.01)
    *A61L 2/24*     (2006.01)
    *A61L 27/04*     (2006.01)
    *A61N 1/372*     (2006.01)
    *A61N 1/30*     (2006.01)

(52) U.S. Cl.
    CPC .......... *A61N 1/325* (2013.01); *A61L 2300/10* (2013.01); *A61N 1/306* (2013.01); *A61N 1/37211* (2013.01)

(58) Field of Classification Search
    CPC .... A61N 1/306; A61N 1/37211; A61N 5/062; A61M 2005/14513; A61M 5/14593; A61M 2037/0007; A61M 5/14276; A61M 5/168; A61M 31/002; A61K 9/0009; A61K 49/0423; A61K 41/0052; A61K 9/5094; A61K 9/20; A61K 9/50; A61F 2/022
    USPC .......................... 604/20, 890.1, 891.1, 892.1
    See application file for complete search history.

(56) References Cited

U.S. PATENT DOCUMENTS

| | | |
|---|---|---|
| 2011/0054612 A1 | 3/2011 | Dehnad et al. |
| 2012/0316655 A1 | 12/2012 | Fuller et al. |
| 2013/0046361 A1 | 2/2013 | Digiore et al. |
| 2013/0140649 A1 | 6/2013 | Rogers et al. |
| 2013/0142885 A1 | 6/2013 | Laurencin et al. |

OTHER PUBLICATIONS

International Preliminary Report on Patentability for Application No. PCT/US2015/022574 dated Oct. 6, 2016.
International Search Report, Jun. 8, 2015, from corresponding International Application No. PCT/US2015/022574.

Example of a meticulous debridement of all affected soft tissues around a knee implant (Kendoff 2012).

Example of more aggressive debridement of infected tissue around a knee implant (Kendoff 2012).

Example of an aggressive debridement of infected tissue around a hip implant (Kendoff 2012).

Demographic characteristics of Medicare patients undergoing surgical procedures in 2001 in the US. As shown in the table, 44% of all surgical procedures performed for these patients involve a hip or knee arthroplasty (Bratzler et al. 2005).

FIG. 4

Types of post-operative infection for joint prostheses, defined by onset time after surgery (Widmer 2001).

| Infection category | Typical onset after surgery | Type | Signs and symptoms | Representative microorganism |
|---|---|---|---|---|
| Early postoperative | <2-4 weeks | Acute (type I) | Persistent pain after surgery, fever, redness, swelling after surgery | *Staphylococcus aureus*, coagulase-negative staphylococci |
| Late chronic | >1 month | Chronic (type II) | Insidious onset, persisting pain after surgery | Coagulase-negative staphylococci, *Propionibacterium* species, anaerobes, *S. aureus* |
| Hematogenous | >2 years | Acute (type III) | Fever, pain, redness, swelling after a long period of wellness | Streptococci, *S. aureus*, gram-negative bacilli |

FIG. 5

The five main steps involved in the formation of bacterial biofilm.

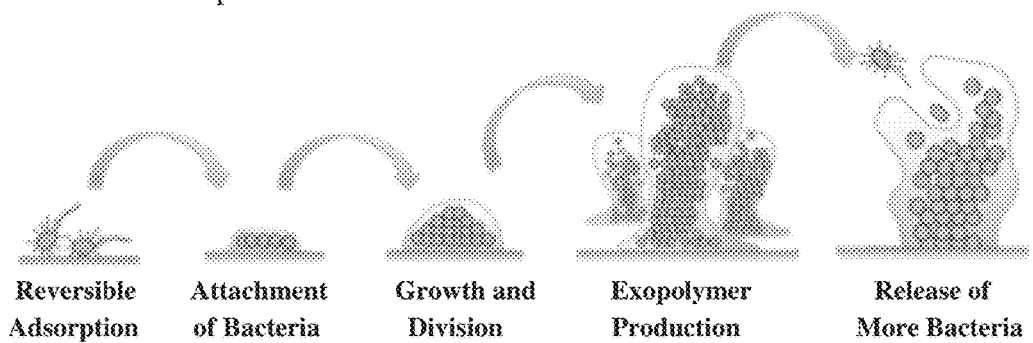

Reversible Adsorption | Attachment of Bacteria | Growth and Division | Exopolymer Production | Release of More Bacteria

FIG. 6

Treatment options for patients with orthopedic device related infection (Widmer 2001).

Option

Debridement with retention of prosthesis and long-term treatment with antimicrobial agents Girdlestone arthroblasty One-stage replacement with or without use of antimicrobial cement and long-term treatment with antimicrobial agents Two-stage replacement with or without use of antimicrobial cement and long-term treatment with antimicrobial agents Suppressive antimicrobial therapy Arthrodeais
Amputation

FIG. 7

Over-the-counter colloidal silver (vitaminshoppe.com).

FIG. 8

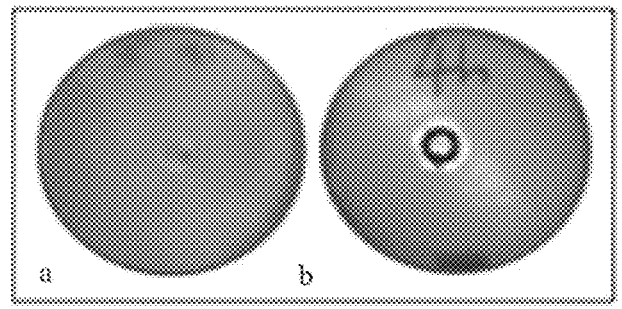

Cultured petri dishes following 4 hours of treatment and 24 hours of incubation. In (b), the silver anodization group, an inhibition zone around the silver washer formed (inhibition zone shown in white, where the washer is outlined in black). In (a), the control stainless steel washer, showed no inhibition zone; only the grey washer can be seen surrounded by bacteria.

FIG. 9

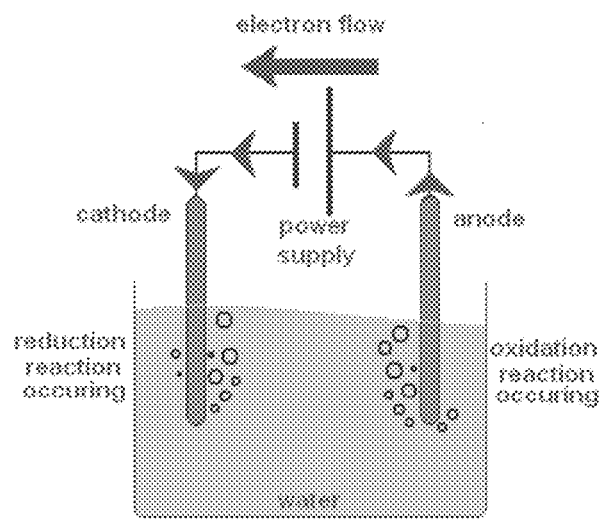

Basic electrolysis setup, where the positive end of a battery is connected to the anode, and the negative end to the cathode, while both electrodes are submerged in an electrolyte bath that allows anions and cations to flow freely.

FIG. 10

Inductance field between two conductors, with silver acting as one of the two conductors.

Eddy Current Resistance on Silver Washer vs. Liftoff

DC electrolysis setup, using Agilent Triple Output DC Power Supply.

Thermo-scientific Ion
Sensitive Electrode

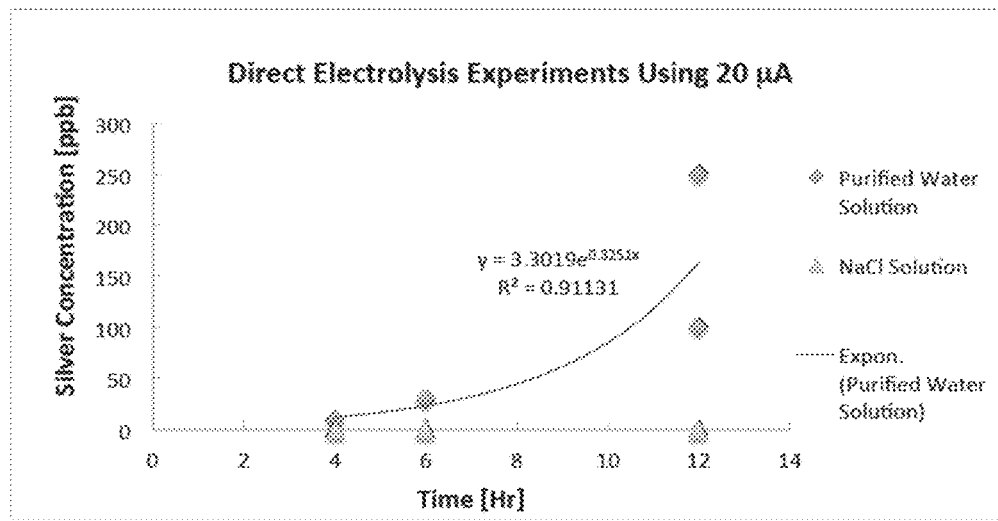

Plot for direct electrolysis experiments in both NaCl solution and purified water solution, both with an applied current of 20 µA. The triangles show the NaCl solution results, which remain at 0ppb at different time periods, while the diamonds show the results in purified water, each for experiments that lasted different lengths of time. As seen in the plot, in purified water, an exponential best fit curve was applied and showed that the concentration of silver ions increases exponentially as time increases, with an R2 value of 0.911.

FIG. 21

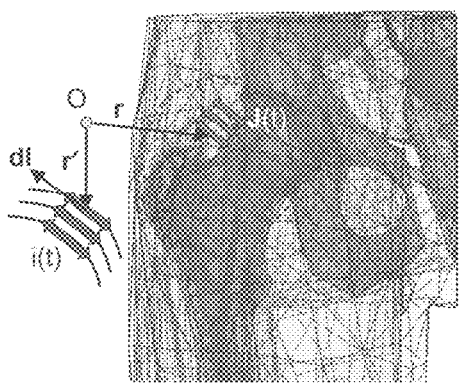

FIG. 22

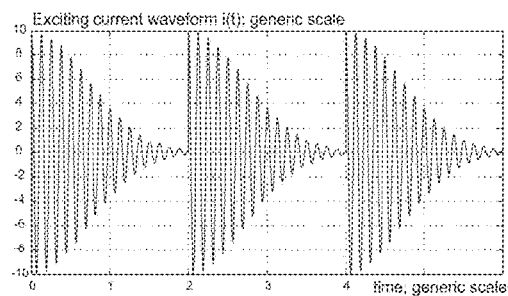 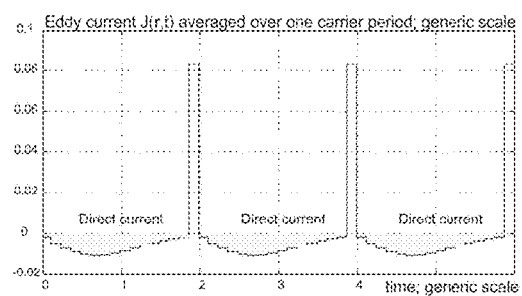
FIG. 23A                    FIG. 23B.

ACTIVATION OF ANTIMICROBIAL AGENTS

CROSS REFERENCE TO RELATED APPLICATIONS

This application is the national phase of International Application No. PCT/US2015/022574, filed on Mar. 25, 2015, which claims the priority benefit of U.S. Provisional Application No. 61/970,783, filed Mar. 26, 2014 and U.S. Provisional Application No. 61/979,866, filed Apr. 15, 2014, both of which applications are hereby incorporated by reference to the maximum extent allowable by law.

BACKGROUND

As the population of late-aged people grows, and bone quality diminishes with age, the need for joint implants increases greatly. With several hundred thousand joint replacement procedures undertaken every year in the US, implant related infection is a complication with consequences for the patient. The rate of post-operative infection for joint replacements is between 0.5-2%, but can increase to over 10% in the field of revision arthroplasty (Kendoff 2012). These surgical procedures can have a major economic impact on the patient, as he or she needs to undergo several additional hospital and clinic visits in addition to the original implant surgery. Since infections may take weeks to months to become detectable, bacteria have time to reproduce and form biofilms. Biofilms are matrix-like layers of exopolymer saccharides that provide a reservoir for new bacteria and allow for persistent infection. Most antibiotics cannot physically break through these matrices and eradicate the bacteria. If this is the case, the patient may need to undergo a more intense management of the infection, which usually involves debridement, irrigation, or removal of the entire implant. Photos of various debridement procedures are shown in FIGS. 1, 2, and 3. Depending on the severity of the infection, local debridement can be performed on the affected local soft tissue around the implant. If late infection occurs and if infection has spread, complete implant removal may be needed. If the entire implant is removed, the patient may be left without a joint for months at a time, perhaps experiencing instability and immobility.

SUMMARY

According to an embodiment, there is provided a method of providing antimicrobial agents, the method comprising supplying a time-varying current through a first conducting material; positioning the first conducting material a distance from a second conducting material, wherein the first conducting material is located outside an organism and the second conducting material is located inside the organism; producing, in the presence of the time-varying current, an electron flow in the second conducting material; and releasing, in the presence of the electron flow, antimicrobial agents from the second conducting material into a region of the organism surrounding the second conducting material.

According to an embodiment, the method further comprises immobilizing the antimicrobial agents in the second conducting material prior to placing it inside the organism.

According to an embodiment, the method further comprises maintaining the time-varying current through the first conducting material for a duration of time to achieve a concentration of the antimicrobial agents in the region.

According to an embodiment, the antimicrobial agents are silver ions.

According to an embodiment, the electron flow in the second conducting material is produced by a wireless mode.

According to an embodiment, the wireless mode is electromagnetic induction.

According to an embodiment, the electron flow in the second conducting material is produced by the first conducting material transmitting a wireless signal and the second conducting material receiving the wireless signal.

According to an embodiment, the antimicrobial agents are activated by the wireless signal.

According to an embodiment, there is provided a device for releasing agents from a medical implant in an organism, the device comprises a power supply configured to produce a time-varying voltage; and a conducting material configured to receive the time-varying voltage across the conducting material, forming a time-varying current through the conducting material; transmit a time-varying magnetic field in response to the time-varying current; and position at a distance from the medical implant, wherein the medical implant receives the time-varying magnetic field and releases the agents based on an induced current in response to the time-varying magnetic field.

According to an embodiment, the device further comprises a mechanism for securing the conducting material to a surface of the organism in proximity to the medical implant, wherein the conducting material conforms to the surface of the organism.

According to an embodiment, the device further comprises a switch configured to control a connection between the power supply and the conducting material, wherein the switch has a connected state where the power supply and the conducting material are connected and a disconnected state where the power supply and the conducting material are disconnected.

According to an embodiment, the agents have antimicrobial properties.

According to an embodiment, the agents are silver ions.

According to an embodiment, the time-varying voltage has a net positive voltage or a net negative voltage.

According to an embodiment, the distance of the conducting material positioned to the medical implant is based on a frequency parameter of the time-varying voltage.

According to an embodiment, the induced current is produced by a wireless mode.

According to an embodiment, the wireless mode is electromagnetic induction.

According to an embodiment, the time-varying magnetic field is a wireless signal transmitted by the conducting material and received by the medical implant.

According to an embodiment, the agents are activated by the wireless signal.

According to an embodiment, there is provided a device comprising a conducting material configured to form a medical implant; receive a time-varying magnetic field; and conduct a current in the presence of the time-varying magnetic field; and a plurality of agents on the conducting material configured to convert to a mobile form in the presence of the current; and release from the conducting material at a rate into a region surrounding at least a portion of the conducting material, wherein the rate and the region are based on at least one parameter of the current.

According to an embodiment, the plurality of agents is further configured to convert to an activated form in the presence of the current.

According to an embodiment, the device further comprises a diode rectifier connected to the conducting material to convert the current in the presence of the time-varying magnetic field into a direct current (DC).

According to an embodiment, the plurality of agents have antimicrobial properties.

According to an embodiment, the mobile form of the plurality of agents is a silver ion.

According to an embodiment, the current is produced by a wireless mode.

According to an embodiment, the wireless mode is electromagnetic induction.

According to an embodiment, the time-varying magnetic field is a wireless signal.

According to an embodiment, at least a portion of the plurality of agents are activated by the wireless signal.

According to an embodiment, there is provided an apparatus comprising a first conducting material configured to receive a time-varying current based on an applied time-varying voltage across the first conducting material; a second conducting material positioned a distance from the first conducting material, wherein a portion of the second conducting material contacts a solution and the second conducting material has an electron flow in the presence of the time-varying current through the first conducting material; and a plurality of agents on the second conducting material, wherein the plurality of agents are configured to release into the solution from the second conducting material in the presence of the electron flow.

According to an embodiment, the apparatus further comprises a switch configured to control the time-varying current in the first conducting material, wherein the switch has a disconnected state that stops current through the first conducting material; and a connected state that allows current through the first conducting material;

According to an embodiment, at least a portion of the plurality of agents, after being released into the solution, return to the second conducting material based on changing at least one parameter of the time-varying voltage.

According to an embodiment, the applied time-varying voltage has a net positive voltage or a net negative voltage.

According to an embodiment, the distance of the first conducting material positioned to the second conducing material is based on a frequency parameter of the applied time-varying voltage.

According to an embodiment, the plurality of agents are further configured to be immobilized on the second conducting material before the electron flow occurs.

According to an embodiment, the second conducting material is a medical implant.

According to an embodiment, the plurality of agents have antimicrobial properties.

According to an embodiment, the plurality of agents are silver ions.

According to an embodiment, the electron flow in the second conducting material is produced by a wireless mode.

According to an embodiment, the wireless mode is electromagnetic induction.

According to an embodiment, wherein the electron flow in the second conducting material is produced by the first conducting material transmitting a wireless signal and the second conducting material receiving the wireless signal.

According to an embodiment, at least a portion of the plurality of agents are activated by the wireless signal.

According to an embodiment, there is provided a system comprising a power source supplying a voltage signal; a waveform generator configured to produce a time-varying voltage from the voltage signal based on at least one parameter; a transmitting electrode configured to receive the time-varying voltage across the transmitting electrode from the waveform generator, wherein a time-varying current through the transmitting electrode forms based on the time-varying voltage; and the transmitting electrode transmits a time-varying magnetic field based on the time-varying current; a receiving electrode positioned to receive the time-varying magnetic field, inducing an electron flow in the receiving electrode based on the time-varying magnetic field; and a plurality of agents released from the receiving electrode in the presence of the electron flow in the receiving electrode.

According to an embodiment, the system further comprises a switch configured to control the time-varying current through the transmitting electrode, wherein the switch has a disconnected state disconnecting the transmitting electrode from receiving the time-varying current and a connected state connecting the transmitting electrode to receive the time-varying current.

According to an embodiment, at least a portion of the plurality of agents, after being released, return to the receiving electrode based on changing at least one parameter of the time-varying voltage.

According to an embodiment, the plurality of agents are immobilized on the receiving electrode prior to positioning it to receive the time-varying magnetic field.

According to an embodiment, the plurality of agents have antimicrobial properties.

According to an embodiment, the electron flow in the receiving electrode is produced by a wireless mode.

According to an embodiment, the wireless mode is electromagnetic induction.

According to an embodiment, the electron flow in the receiving electrode is produced by the transmitting electrode transmitting a wireless signal and the receiving electrode receiving the wireless signal.

According to an embodiment, at least a portion of the plurality of agents are activated by the wireless signal.

BRIEF DESCRIPTION OF DRAWINGS

FIG. 4 illustrates demographic characteristics of Medicare patients undergoing surgical procedures in 2001 in the US. As shown in the table, 44% of all surgical procedures performed for these patients involve a hip or knee arthroplasty (Bratzler et al. 2005).

FIG. 5 illustrates types of post-operative infection for joint prostheses, defined by onset time after surgery (Widmer 2001).

FIG. 6 illustrates the five main steps involved in the formation of bacterial biofilm.

FIG. 7 illustrates treatment options for patients with orthopedic device related infection (Widmer 2001).

FIG. 8 illustrates an over-the-counter colloidal silver (vitaminshoppe.com).

FIG. 9 illustrates cultured petri dishes following 4 hours of treatment and 24 hours of incubation. In (b), the silver anodization group, an inhibition zone around the silver washer formed (inhibition zone shown in white, where the washer is outlined in black). In (a), the control stainless steel washer, showed no inhibition zone; only the grey washer can be seen surrounded by bacteria.

FIG. 10 illustrates a basic electrolysis setup, where the positive end of a battery is connected to the anode, and the negative end to the cathode, while both electrodes are submerged in an electrolyte bath that allows anions and cations to flow freely.

FIG. 21 is a plot for direct electrolysis experiments in both NaCl solution and purified water solution, both with an applied current of 20 µA. The green triangles show the NaCl solution results, which remain at 0 ppb at different time periods, while the blue diamonds show the results in purified water, each for experiments that lasted different lengths of time. As seen in the plot, in purified water, an exponential best fit curve was applied and showed that the concentration of silver ions increases exponentially as time increases, with an R2 value of 0.911.

FIG. 22 illustrates a section of FEM compatible femur phantom (custom modification of ANSYS human body model, no implant) and parameters of the eddy current excitation.

FIGS. 23A and 23B illustrate exciting current and the eddy current density averaged over a carrier period.

DETAILED DESCRIPTION

Figure 1:
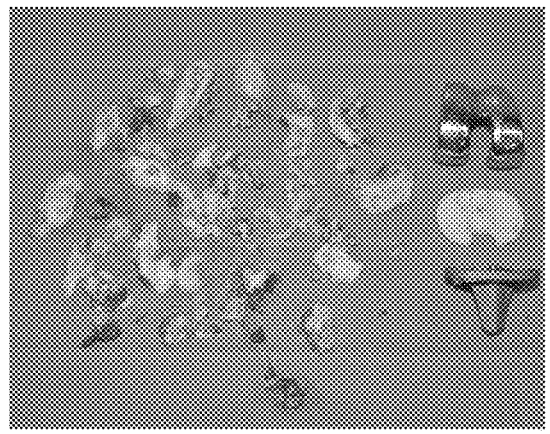
FIG. 1 illustrates an example of a meticulous debridement of all affected soft tissues around a knee implant (Kendoff 2012).
Figure 2:
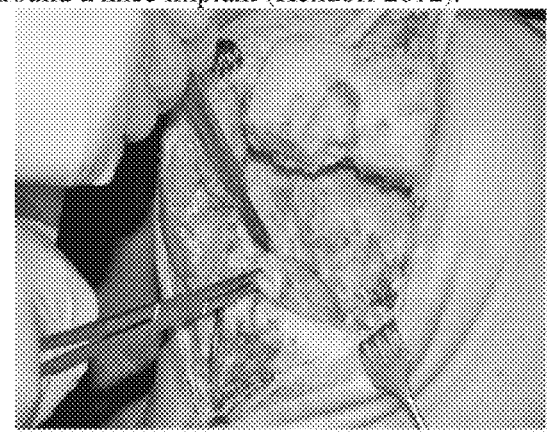
FIG. 2 illustrates an example of more aggressive debridement of infected tissue around a knee implant (Kendoff 2012).
Figure 3:
FIG. 3 illustrates an example of an aggressive debridement of infected tissue around a hip implant (Kendoff 2012).

The average period of time between colonization of bacteria and clinically detectable symptoms of infection can last anywhere from weeks to years. This allows ample time for biofilm formation, which may cause antibiotics to be ineffective against the infection. Thus, the current method for removing biofilm and infection is debridement of the implant, or complete removal of the implant. In order to avoid these surgical procedures, modifications have been made to the antibiotic regimen during the perioperative period, and also to implant surfaces that involve new and innovative implant coatings. Some implants are now coated with antibiotics or other bactericidal agents in order to impede biofilm formation. These coatings should biocompatible, have a low toxicity, and be able to release an optimal dose of antibiotics for a sufficient period of time. Some types of coatings include biodegradable solutions containing the antibiotics gentamicin or teicoplanin (Gollwitzer, et al. 2003), silver-containing hydroxyapatite (Chen, et al. 2006), or carbonated hydroxyapatite coatings containing amoxicillin, gentamicin, or carbenicillin (Stigter, et al. 2004). However, the main issue with all of these types of coatings is the release of antibiotics over a sustained period of time. While these coatings may be able to release antibiotics for a few months to a year, the patient becomes susceptible to infection as soon as the coating wears off. Therefore, an implant coating is needed that is capable of actively releasing optimal doses of microbicidal agents to both prevent bacterial biofilm formation and eradicate any existing biofilms, and can halt the release of these agents to avoid any toxic effects or bacterial resistance, all over the entire period that a patient has the implant. Silver is known as an antimicrobial agent, as silver ions $(Ag+)$ interact with structural components of pathogenic microorganisms, eradicating the organism. The anodization of silver has previously been shown to reduce bacterial growth, and thus could be used as the basis of an innovative implant coating. Therefore, embodiments provide a silver coated implant that is able to actively release silver ions, using a wireless electrolysis system in-vivo.

First, the background of previous research and knowledge needed to understand the principles of both joint prostheses, and the basis for the electrical components of this project will be described. Next, methods that comprise a system in which silver ions can be released into solution via wireless electrolysis will be described. One method used to calculate the concentration of silver ions in solution is the use of an ion sensitive electrode, or ISE, that specifically measures silver ion concentration. Direct, wired electrolysis will first be used to reproduce previous experimentation, and then methods allowing wireless electrolysis to occur will be explained. The principle of induction is the basis of all wireless methods, which will be explained mathematically as well. Devices that can be used in a clinical setting will also be described.

The inventors are not aware of implant coatings that have the ability to release antimicrobial agents over a sustained period of time, for both preventing and eradicating biofilm formation around joint implant surfaces. Implant infection has much too high an occurrence rate to not invest in better technology to avoid implant infection. Embodiments are directed to a novel method of creating implant coatings that can actively release antimicrobial agents as needed, at the flip of a switch. Embodiments provide a wireless method of releasing microbicidal agents within the body, without any hospital visits or additional costs to the patient, thus potentially reducing the rate of post-operative infection.

Bio-implants, such as joint prostheses, act as passive surfaces on which bacterial adhesion can potentially lead to deep body infection (Secinti, et al. 2008). As the population ages and bone quality decreases, the need for these joint prostheses to replace bones in the hip or knee is increasing. However, surgical site infections are common, and can be a major contributor to patient injury, health care costs, and even mortality. According to Bratzler et al. (2005), more than 2% of operations performed nationwide are complicated by post-operative infection, and these surgical site infections increase hospital charges and the hospital stay for patients by an average of seven days. Research findings by Bratzler, et al. (2005) suggest that out of a random sample of 34,133 Medicare patients undergoing surgery, 15,030 of those patients were receiving a hip or knee arthroplasty, as shown in FIG. 4. Furthermore, in 1996 about 800,000 hip or knee arthroplasties were done in the United States alone (Cataldo, et al. 2010). When a joint replacement surgery is performed, the most serious complication is infection, with a high 1.5-2.5% incidence rate for primary infections, and up to 20% for adjustment procedures, causing an estimated cost of $250 million per year in the United States (Cataldo et al. 2010).

Prosthetic joint infection is commonly classified by the time of onset after surgery (Esposito & Leone 2008). Early postoperative infections can be defined as having an onset time of two to four weeks after surgery takes place, and are usually acquired during the implantation procedure. Delayed manifestation, or late chronic infection, is defined as having an onset time of at least one month after surgery, and is also thought to be caused by infection acquired during the procedure. Lastly, late manifestation occurs at least two years after surgery, and is caused by haematogenous seeding, which sometimes initiates from unknown causes (Dabasia et al. 2009). A table describing these three conditions is shown in FIG. 5. The two most common bacteria found in infections are *Staphylococcus aureus* and *Staphylococcus epidermis*, accounting for approximately 65% of both early and late infections (Esposito & Leone, 2008). These bacteria have the ability to form a biofilm, or a structure containing a self-organized group of microorganisms that create a matrix-like layer of exopolymer saccharides. The steps involved in biofilm formation are shown in FIG. 6. These colonies can occur either at the time of implant surgery, or as a result of haematogenous seeding. Bacteria within a biofilm have increased antimicrobial resistance due to the extracellular matrix. Nutrient and oxygen depletion within the matrix also causes the microorganisms to enter a non-growth phase, causing them to be less susceptible to antimicrobials (Esposito & Leone 2008).

Antimicrobial therapy is important for any prosthetic joint surgery. Currently, antibiotic prophylaxis before implantation surgery is often used and can be effective in reducing the risk of subsequent infection, especially in patients with other risk factors such as diabetes, drug or radiation induced immunosuppression, HIV, or previous joint infections (Cataldo, et al. 2010). However, patients who undergo prophylaxis are still prescribed an antibiotic regimen to fight post-surgery infection, including intravenous treatment followed by oral treatment. Antibiotics administered systemically are shown to be less effective against infections linked with implants (Hetrick & Schoenfisch, 2006). When antibiotics can no longer cure the implant associated infection, treatment may be achieved by removal of the implant, debridement of devitalized tissue, and long-term antimicrobial treatment. This method may be associated with loss of bone stock, immobilization, and perioperative complications (Trebse, et al. 2005). A list of options for patients who contract infection is shown in FIG. 7. A new type of implant structure that has both mechanical integrity and antimicrobial activity could prove beneficial to the prosthetic implant field. If this implant contained a unique coating that released antimicrobial elements over time in-vivo, infections could be prevented, or suppressed as they occur.

Improved implant stability may be achieved using several types of implant materials, while different implant coatings help to achieve biocompatibility and potentially post-operative antimicrobial activity. Currently, the most commonly used materials in orthopedic implants are metals and polyethylene. When metals and polyethylene are combined, stability is improved, and implant wear is reduced. Polyethylene-on-metal implants also allow patients to have the least amount of excess metal ion levels in urine (MacDonald et al. 2003). Common metals used include stainless steel, titanium alloys, and titanium. Clinical studies have shown that movement between the implant surface and tissue around it gives rise to liquid filled capsule formations, which is more prevalent in stainless steel implants than in titanium implants (Richards et al. 2002). Titanium and titanium alloys have further been shown to have strong mechanical properties and high levels of biocompatibility, but unique coatings are still necessary for the antimicrobial aspect of the implant (Zhao, et al. 2009). Many of these types implants have the potential of also being coated with antibiotics such as cephalothin, carbenicillin, amoxicillin, cefamandol, tobramycin, gentamicin, and vanocomysin (Stigter, et al. 2004). Some coatings have combined silver with antibiotics like oxacillin or amikacin using an organic solvent and have been shown to have significantly fewer bacterial colonies around the implant after one week (Benvenisty, et al. 1988). However, other studies with solely silver coated grafts or implants have shown less favorable results (Gao, et al. 2010), which could be due to the fact that there is no mechanism for the release of silver ions from the implant surface. While some antimicrobial coatings have shown promise for short periods of time, none have the ability to release antimicrobial agents for a sustained period of time, to both prevent and eradicate biofilm over the entire period that a patient has a joint implant.

Silver is known for its antimicrobial properties. Currently, silver is still used within implant or graft coatings, as stated above, and for fighting antibiotic resistant bacteria in wound care (Percival, et al. 2012). As bacteria have become more resistant to antibiotics, several scientists have turned to silver to solve this issue. The Collins Lab at Boston University has performed several studies showing that silver enhances antibiotic activity against gramnegative bacteria (Morones-Ramirez, et al. 2013). The exact mechanism behind this phenomenon is still unclear, but this study led by Morones-Ramirez has shown that silver disrupts multiple bacterial cellular processes, including disulfide bond formation, iron together, cause the bacterial membrane to become more permeable, which then allows antibiotics to be more efficient. Silver is even used on a daily basis by many to kill germs in teeth and gums, on the face to treat acne, on the skin for bug bites or burns, and for eye and ear infections. A typical over-the-counter colloidal silver product is shown in FIG. 8. Colloidal silver comprises a solution containing suspended particles that range in size from 1 nanometer to 1 micron, in pure water. Ionic silver, on the other hand, is a solution in which silver ions ($Ag^+$) are suspended. These ions have a diameter of 0.230 nanometers. Studies have shown that a concentration of only 15 ppb of $Ag^+$ ions is sufficient to eradicate several strains of bacteria.

A wired, in-vitro electrolysis system has been previously created in the Nazarian lab at Beth Israel Deaconess Medical Center that is capable of anodization and the release of $Ag^+$ ions from a silver coated surface. Silver coated washers were implanted into a bacterial culture of *Staphylococcus aureus* and treated with 20 µA of current for a 4-hour interval. Stainless steel washers were used as controls. After treatment, the samples went through a 24-hour incubation and then were examined for bactericidal effects. Circular inhibition zones around the washer with no bacteria present visually were considered a positive result. The results of this experiment showed that the stainless steel control group had negative results with bacteria growing all around the washer, while the silver coated washer had positive results, with a circular area of no bacterial growth around the washer, as seen in FIG. 9. Thus, these preliminary results obtained from previous studies performed in the Nazarian lab indicate that $A_g$+ ions can indeed have bactericidal effects against bacterial strains such as *Staphylococcus aureus*, and that silver coated implants with an electrolysis system could potentially be used to prevent and terminate bacterial infection on joint prosthesis.

Figure 11:
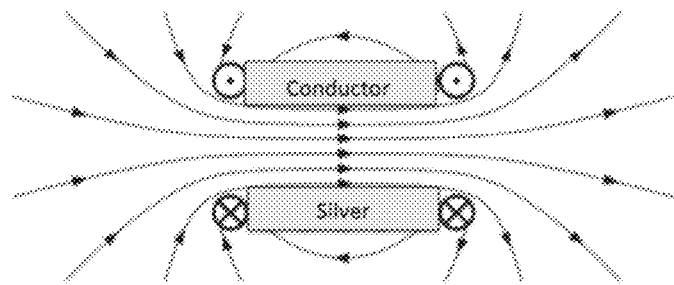
FIG. 11 illustrates an inductance field between two conductors, with silver acting as one of the two conductors

Electrolysis is the chemical process of using a direct electric (DC) current to drive an otherwise non-spontaneous chemical reaction. The process involves an anode and a cathode to be submerged in an electrolyte buffer, which allows electrons to flow from the anode to the cathode. This process is a common way to electroplate metals onto other metals. FIG. 10 shows a simple electrolysis setup for reference. The backwards process, often called "reverse electrolysis," involves the freeing of metals, releasing ions back into the electrolyte, and is the literal reverse of the electrolysis process. Reverse electrolysis is a feasible way to induce the release of silver ($Ag^+$) ions from an implant covered with a silver plating, but the tests that have been conducted using silver as the antibiotic agent have all been in laboratory conditions where the silver coated the implant, which is not ideal. Thus, an embodiment provides a method that wirelessly induces electrolysis of silver ions so that patients can receive treatment non-invasively. The wireless electrolysis system revolves around the property of inductance. This property shows that a change in current within a conductor allows for an electromagnetic force to occur in the conductor itself, and also in any nearby conductors. This is due to the fact that a steady current creates a magnetic field, and also that a time varying magnetic field induces a voltage within nearby conductors, creating a minor current in the second conductor. A graphical description of this occurrence is shown in FIG. 11, where the second conductor is silver. A major obstacle with this method is that electrolysis relies on DC currents, but inductance relies on alternating, or AC currents. Different methods will be explained and described in detail in the following methods section. Embodiments may reduce postoperative infections and patients could undergo infection treatment in the comfort of their own home, also greatly reducing medical costs.

Figure 12:
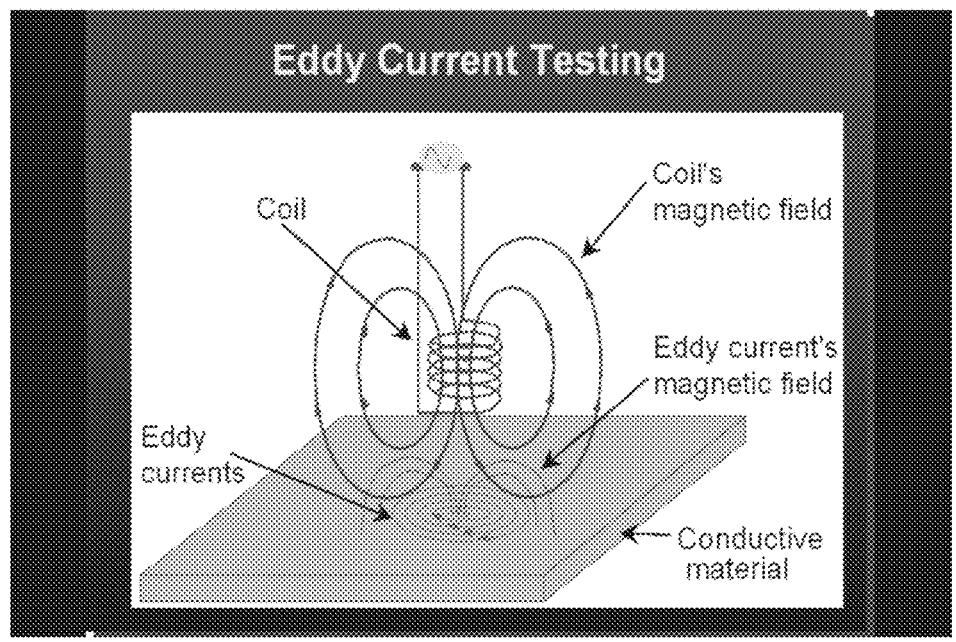
FIG. 12 illustrates a simplified view of how eddy currents are induced. A transducer (coil of wires, solenoid, conducting strip of metal) with an AC current running through it will produce a magnetic field of changing value. As the magnetic field changes, a current is produced on the surface of a nearby conductive metal such as silver.

The theory behind the described embodiments makes use of the principles of inductance and eddy currents. An external inductor, a strip of conducting material, will have an AC current running through it. When the external source is near the silver plating, the changing magnetic field caused by the constantly-changing current flowing through the conductor will cause eddy currents to flow on the surface of the silver. An example of the principles of eddy currents is shown in FIG. 12, with a coil of wires acting as the inductor in place of a strip of conducting material. The eddy currents induced on the surface of the silver plating will cause reverse electrolysis to occur, and a net flow of current in one direction will allow silver ions to serve their purpose as microbial agents.

The inventors have recognized and appreciated that an important aspect of a wireless electrolysis system is choosing the proper waveform to go through the conducting material. Electrolysis usually relies on direct current passing through the electrodes, but wireless induction produces an alternating current in response to the ever-changing current passing through the conductor to create an EMF on a nearby metal surface. The voltage that is induced is a result of the cumulative sum of the derivative of the signal that passes through the conducting material. A simple sine wave could be induced, but the net flow of electrons would be zero, which in theory will produce no electrolysis; an alternating-current signal with a net positive or negative voltage is needed to ensure electron flow between electrodes. A cosine function is combined with a Gaussian error function to produce the waveform, because its derivative has the desired behavior. The general form of the equation is: $x(t) = e^{-at^2} * \cos(\omega t)$, where t is the independent time variable while $\alpha$ and $\omega$ are parameters that may be changed. After outputting various forms of this equation through a data acquisition (DAQ) board to an oscilloscope to observe the waveform, it became clear that $\omega$ represented the frequency of the wave, and $\alpha$ changed how much of the Gaussian error was enveloped by the cosine wave and thus included in contributing to inducing a current. The frequency was set to 100 Hz, and optimization techniques in MATLAB showed that a value of a=0.000001 produced a derivative with the largest absolute value. The final waveform used is: $x(t) = e^{-000001 t^2} * 10 \cos(100t)$. The scale factor in front of the cosine function increases the amplitude of the waveform to match the maximum output allowed by the DAQ board (20 Volts peak-to-peak, from −10 to +10 Volts). The derivative of the waveform output, which defines the EMF induced on the silver plating, was determined to be: $[(2.5388936*10^{1085736208}i)*\text{erf}(50,000-(0.001i)t)-\text{erf}(50,000+(0.001 1i)]$, where erf is the error function $e^{-000001 t^2}$ that was used in the original waveform. Only the first full second of the waveform was used as the output, since after that first second the value of the derivative was too small to make any significant contribution to the induced EMF, so the first one-second interval of the signal was repeated continuously for the duration of testing. The value of the derivative over that interval was evaluated to be 0.0520 A/s, meaning there would be a net nonzero flow of ions, which was verified in MATLAB.

Figure 13:
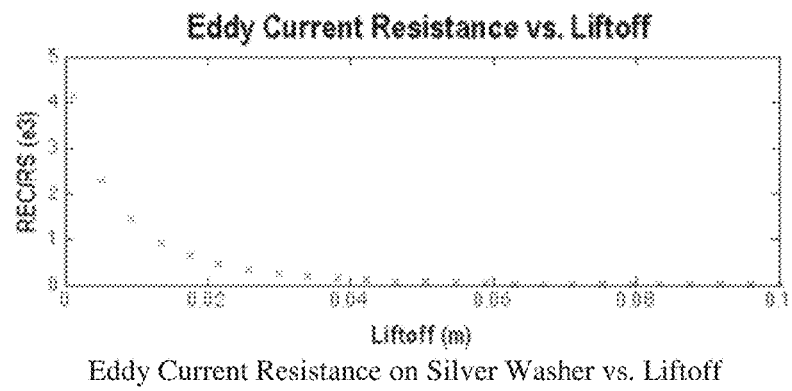
FIG. 13 illustrates Eddy Current Resistance on Silver Washer vs. Liftoff

The second part of the system that required mathematical proof was the induction value of the conducting material. From previous work on surface wave acoustics caused by electromagnetic transducers (Szabo 1977), it was determined that inductance of the conductor is represented as:

$$L_{E\eta} = \frac{\mu_0 l}{\pi N_S^\eta} \sum_{n=1}^{\infty} \left(\frac{1}{n}\right) \text{sinc}^2\left(\frac{nS}{2b}\right)(1 + \eta\cos n\pi)/2 \cdot [1 - \exp(2n\pi G/b)]$$

where S and l are the conductor's width and length, respectively, b is the spacing between conducting strips, and G is the spacing between the conductor and surface of the silver. $\mu = 4*\pi e-7$ [H/m] and is the constant for permeability of free space. The equation $$R_{EC}/R_S = \frac{N_S l}{b}\sum_{n=0}^{\infty} \text{sinc}\left(\frac{nS}{2b}\right)\cdot \exp\left(\frac{-n2\pi G}{b}\right)$$

was used to optimize the amount of resistance encountered from the eddy current that is produced on the silver, based on the same variables as the previous equation. Using the liftoff value G as the independent variable, the relationship of liftoff with eddy current resistance can be seen in FIG. 13. As can be seen in the figure, the eddy current resistance drops off to nearly zero as the liftoff value becomes greater than 0.02 meters. Since the conducting material is one flat strip of copper, many terms can be extracted out of the original equation for inductance, such as the spacing between strips, b, which essentially becomes infinite because only one strip is used, and the need for a geometric sum also disappears. The reduced and simplified equation for the inductance of the copper strip is:

$$L = 0.0002 * l * \left[ \ln\left(\frac{2l}{wG}\right) + 0.5 + 0.2235\left(\frac{wG}{l}\right) \right]$$

where l, w, and G are the length, width, and liftoff of the copper strip, respectively, with all units in mm. The width was chosen to be 25 mm to ensure that it covered all of the silver during testing, the length was 150 mm to be able to span the petri dishes without falling in, and the liftoff spacing was 6 mm (from the top of the petri dish to the bottom laid with silver), to yield an induction value of 84 nH. It was then possible to deduct the EMF produced on the surface of the silver through the equation:

$$v_m = N_m \frac{d\Phi_m}{dt} = \sum_{n=1}^{k} L_{m,n} \frac{di_n}{dt};$$

where L is the induction value of the copper strip (84 nH) and the derivative of the current over a one-second interval is 0.0520 A/s, yielding an induced voltage of 4.368e−9 V (4.369 nV).

Figure 14:
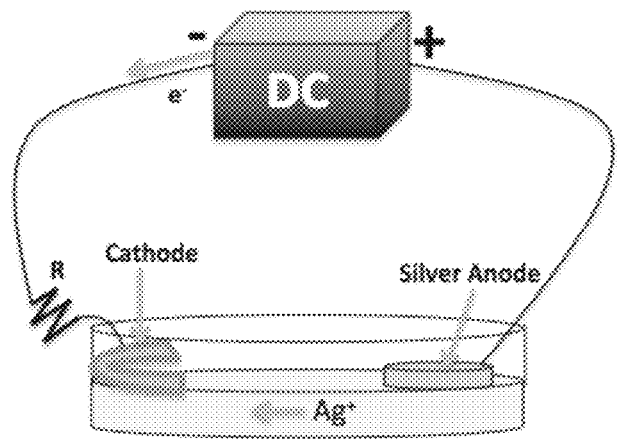
FIG. 14 illustrates a DC electrolysis setup, using an Agilent Triple Output DC Power Supply.
Figure 15:
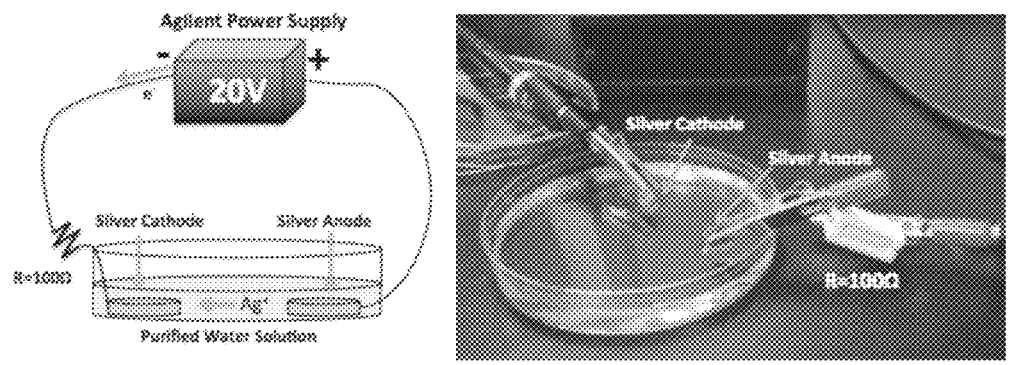
FIG. 15 illustrates a high output direct electrolysis setup using an Agilent Triple Output DC Power Supply.

All wired and wireless systems were tested using 99.99% pure silver washers of approximately five mm in diameter. The first electrolysis experiments run were wired, DC-current, silver electrolysis setups. The goal of these two tests was to reproduce the initial electrolysis experiments done by others to serve as the optimal standard by which we can test the efficacy of further electrolysis runs. We aimed to reproduce the current of 20 μA used in the initial experiments using an Agilent E3630A Triple Output DC Power Supply. Two different kinds of resistors, with resistance values of 1600Ω and 10 kΩ, were used, requiring the DC voltage outputs of the two experiments to be 0.032V and 0.2V, respectively, according to the law that V=IR for a simple resistance circuit. This electrolysis circuit is shown in FIG. 14. Originally, the electrolyte used in the electrolysis experiments was a 0.9% NaCl solution, but further research showed that any silver ions being freed from the washers were not remaining as free ions but rather combining with the chloride ions in the solution to form the unusable product, AgCl. Silver chloride does not have known antimicrobial properties and thus the initial setup was yielding very small amounts of silver chloride instead of allowing the silver ions to work as planned. Further research showed that electrolytically isolated silver is best formed in deionized water. Thus, at the beginning of this testing period, a high output direct electrolysis experiment was run using purified water as the solution in which the silver disks are contained. Using the Agilent E3630A Triple Output DC Power Supply, 20V was applied to the wired setup containing a 100S2 resistor, allowing for 200 mA to be applied to the silver disks. This setup is shown in FIG. 15. Using the Triple Output DC Power Supply, 2V was applied to the wired setup containing a 100,000S2 resistor, allowing for 20 μA to be applied to the silver disks. Tests were run to apply a direct current of 1 mA (using 1.6V and a 1600S2 resistor) to the silver disks, since this is an upper threshold of what the human body can handle comfortably, and in case 20 μA did not produce a large enough ion concentration of silver to be read. Both experiments ran for a 4-hour period, and successive trials were run for 12-hour periods.

Figure 16:
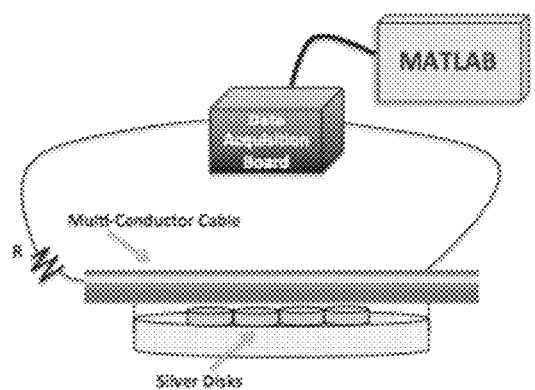
FIG. 16 illustrates a wireless electrolysis setup with multi-conductor cable and modulated waveform as an output from MATLAB.
Figure 17:
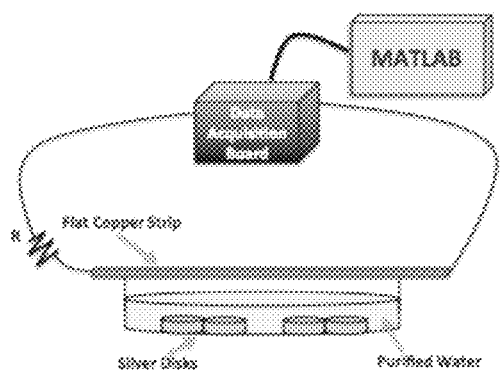
FIG. 17 illustrates a wireless electrolysis setup with a flat copper strip as the conductor, and modulated waveform as an output from MATLAB.
Figure 18:
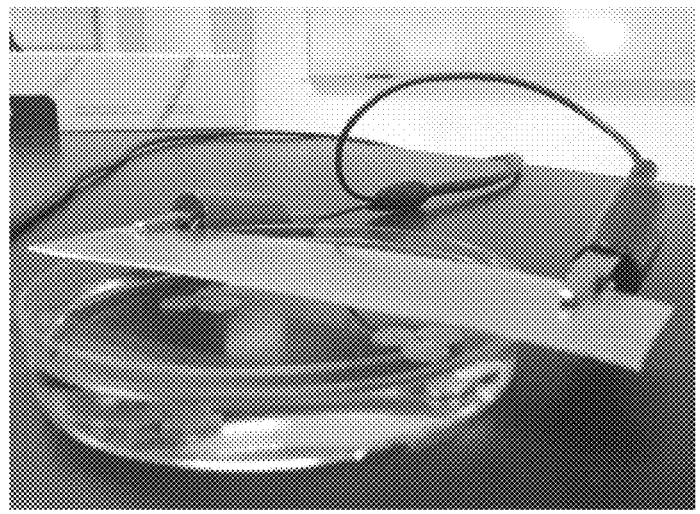
FIG. 18 illustrates a wireless electrolysis with flat copper strip as the conductor, placed 6 mm above silver disks.
Figure 19:
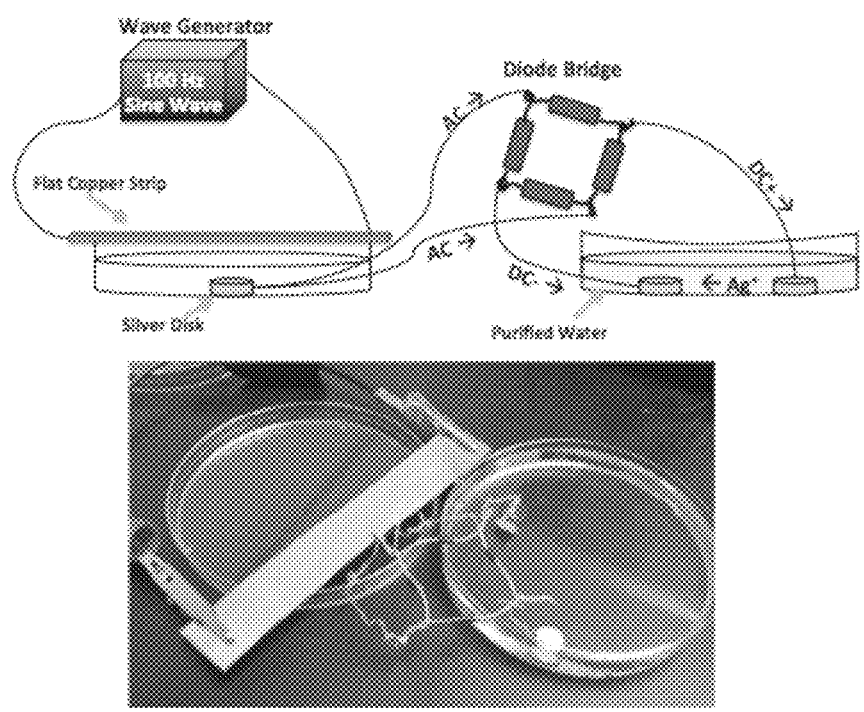
FIG. 19 illustrates an electrolysis setup using a diode bridge, and wirelessly transmitted AC signal.
Figure 20:
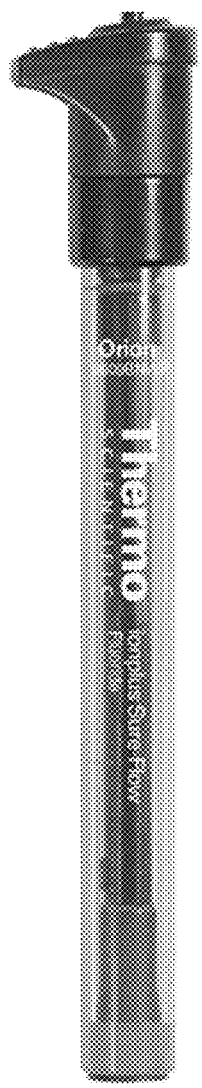
FIG. 20 illustrates a thermo-scientific Ion Sensitive Electrode

The wireless systems included silver washers in a petri dish except instead of a power source connected directly to the electrodes, a conducting material was placed at the top of the petri dish and had a signal passed through it to induce a mirror current and EMF on the surface of the silver washers. Before the modulated waveform was used, simple sine waves of varying frequencies (8 MHz, 2 MHz, and 1 kHz) from an Agilent Waveform Generator were tried, under the premise that although the net current flow is zero, stray silver ions might be released as the silver washers acting as the anode and cathode switch every half-cycle. It became clear that doing so would not produce enough silver to have a significant effect on bacteria, and thus it became pertinent to use the modulated waveform by using a DAQ board to pass a signal from MATLAB to the conductor in series with a resistor to prevent the circuit from shorting-out. Using both modulated waveforms and simple sine waves, wireless testing was conducted over 4-hour and 12-hour periods of time. The conducting material originally used was a flat multi-conductor cable, 8 small wires in parallel passing over the silver washers. This setup is modeled in FIG. 16. After looking into how to maximize the inductive properties of the conducting material used, it was realized that one wide, flat piece of conductor would have a larger effect than 8 thin, circular wires with insulation around them, which is why the copper strip was used. Copper's conductive properties are well known, and it was also much easier to determine the skin depth. The skin depth of a conductor is related to the skin effect, which is the tendency for an alternating current to become distributed on the surface of a conducting material, the crux of the wireless setup. The skin depth can be calculated by using the equation $$\delta = \sqrt{\frac{2p}{\omega \mu}},$$

where p is the resistivity of the conductor, ω is the angular frequency, and μ is the absolute magnetic permeability of the conductor, and it is the distance from the conductor at which the current density has dropped to 1/e (~0.37) of its original value. Since the EMF induced by the copper strip was calculated to be 4.369 nV, and the liftoff between the conductor and the silver washers was 6 mm, a frequency of 100 Hz was used in the modulated signal to yield a skin depth of approximately 6.5 mm so that we can know the EMF on the silver is 1/e times its max value (4.369 nV/e=1.607 nV on silver surface). The final wireless setup using MATLAB can be seen in FIGS. 17 and 18. Using a diode rectifier was also considered, where a diode bridge was built using four diodes to convert an AC signal to a DC one. The thought behind this was that if a modulated signal would not produce a net flow of ions, it would be possible for a simple sine wave to induce an AC current onto some metal inside the body that would input the induced current to two ends of the diode bridge while the other two ends would output a DC current connected to the silver electrodes as in the Wired Systems to allow for traditional electrolysis to take place. FIG. 19 shows the bridge's use as planned in a human body, with an external conductor to create an AC current and the internal diode bridge and silver component to convert the induced current to a DC one and electrolyze ions.

To test concentrations of silver produced in the electrolysis experiments and to verify that the system was working, the Thermo Scientific Orion Silver/Sulfide Electrode was used, capable of detecting concentrations of silver as low as 0.01 ppm (10 ppb). The electrode was connected to a Thenno Scientific pH/ISE meter to be able to read out concentration values. The electrode had to be calibrated using Silver Nitrate standards before properly being used. Solutions of Silver Nitrate were diluted from 0.1 M Silver Nitrate to yield concentrations of $10^{-2}$, $10^{-3}$, $10^{-4}$, $10^{-5}$, $10^{-6}$, and $10^{-7}$ M standards. The electrode had to be calibrated by filling it with a reference solution provided by Thenno Scientific (Optimum Result Solution C) and then by being placed in up to five of the silver nitrate standards, from the least concentrated to the most. The electrode would read the concentration of the solutions automatically, but it could be manually adjusted if the readings are not precise, and then it would create a calibration curve equating the mV readings it detected in a solution to a concentration of silver ions. To test solutions, the electrode simply had to be placed in the solution for a few seconds while the reading was stabilized, and the Thermo Scientific meter read out the detected quantity of silver.

As previously discussed, wired electrolysis experiments were conducted in order to verify the functionality of the silver electrode, and also to replicate past experiments performed for this project, which showed bacterial inhibition zones when 20 µA of direct current was applied directly to silver washers. As seen in Table 1, in the first round of experiments in which NaCl was used as the electrolytic solution for electrolysis, 0 ppb of $Ag^+$ was detected when 20 µA of current was applied for 12, 22, and even 40 hours. Once purified water was used as the solution, a verification experiment showed that 200 mA of current applied for only 20 minutes allowed the electrode to read 700 ppb of $Ag^+$. Thereafter, when 20 µA of current was applied for 4, 6, 12, and 20 hours, the concentration of $Ag^+$ detected by the electrode was 10, 30, 100, and 250 ppb, respectively (Table 1).

TABLE 1

Results for control experiments using direct electrolysis. As shown in experiments 5, 7, 10, and 14, when NaCl was used as the solution medium, no silver was recorded with the ISE. Once purified water was used, silver concentrations became apparent, and increased with both time and current applied to the system.
Direct Electrolysis Experiments

| Date | Exp. # | Current | Solution Medium | Time Period | [$Ag^+$] in ppb |
|---|---|---|---|---|---|
| Oct. 22 | 5 | 20 µA | NaCl | 12 Hours | 0 |
| Oct. 25 | 7 | 20 µA | NaCl | 22 Hours | 0 |
| Oct. 26 | 10 | 20 µA | NaCl | 40 Hours | 0 |
| Nov. 16 | 14 | 200 mA | Purified Water | 20 Min | 700 |
| Nov. 18 | 17 | 20 µA | Purified Water | 4 Hours | 10 |
| Nov. 22 | 25 | 20 µA | Purified Water | 6 Hours | 30 |
| Nov. 23 | 31 | 20 µA | Purified Water | 12 Hours | 100 |
| Nov. 23 | 30 | 20 µA | Purified Water | 12 Hours | 250 |

In FIG. 21, the direct electrolysis results are plotted for experiments performed in NaCl solution as well as in purified water solution, for trials that ran for different time periods. An exponential best fit line was applied to the results ran in purified water, and was found to have a very nice fit with the equation $y=3.302e^{033x}$, with an $R^2$ value of 0.911.

In all wireless experiments discussed below, a modulated waveform was created in MATLAB, using the first one-second period of the equation $e^{0001t2}$ 10 cos(100t), and repeating through a loop for the full period of time shown in Table 2. This equation allowed for a wave with 100 Hz frequency, maximum peak-peak voltage of 20V, and a net negative integral. Except for the first experiment, which used a multi-conductor cable, this modulated waveform was applied to a 25 mm wide copper strip that covered the entire surface area of the silver disks. As seen in Table 2, the first few experiments using NaCl as the electrolytic solution for electrolysis were shown to be unproductive, yielding 0ppb of $Ag^+$. Once purified water was used, concentrations of $Ag^+$ were recorded, but only after at least 6 hours. After 12 hours, 25 and 40ppb were measured, after 14 hours 60ppb was measured, and after 20 hours 180 ppb was measured (corrected by control values).

TABLE 2

Results for wireless experiments using a MATLAB output of a modulated waveform. As shown in experiments 4 and 11, when NaCl was used as the solution medium, no silver was recorded with the ISE. Once purified water was used, silver concentrations became apparent, and increased as the waveform was applied for longer periods of time.
Wireless Electrolysis Experiments with Modulated Waveform

| Date | Exp. # | Solution Medium | Conductor | Time Period | [$Ag^+$] in ppb |
|---|---|---|---|---|---|
| Oct. 7 | 4 | NaCl | Multi-Conductor Cable | 5 Hours | 0 |
| Oct. 28 | 11 | NaCl | Copper Strip | 5 Hours | 0 |
| Nov. 22 | 22 | Purified Water | Copper Strip | 6 Hours | 0 |
| Nov. 23 | 26 | Purified Water | Copper Strip | 12 Hours | 25 |
| Nov. 23 | 27 | Purified Water | Copper Strip | 12 Hours | 40 |
| Nov. 26 | 32 | Purified Water | Copper Strip | 14 Hours | 60 |
| Dec. 3 | 36 | Purified Water | Copper Strip | 20 Hours | 180 |

Data points from wireless electrolysis experiments using a modulated waveform are shown in FIG. 22. A best fit polynomial was applied to the data, and it was determined that a $2n^d$ degree polynomial created the best fit with an equation of $y=0.92x^2-10.97x+32.65$, which allowed for an $R^2$ value of 0.99, which shows an extremely accurate fit. An independent t-test was performed comparing the data between the wired electrolysis experiments and the wireless electrolysis experiments to determine if the two group's averages are unlikely to have occurred because of random chance within the sample selection. The null hypothesis in this case is that the wired and wireless independent experiments are distinguishable. The results of this t-test are shown in Table 3, where a p-value of 0.586 was calculated using a 95% confidence interval. This means that since the p-value is greater than 0.05, we can reject the null hypothesis that states the wired and wireless systems are distinguishable with respect to effectiveness. Therefore, the wired and wireless systems are not distinguishable and gave similar results. Furthermore, the t-value calculated is 0.57, which is less than the t-value at even the most stringent confidence levels, showing that there is no significant difference between the wired and wireless $Ag^+$ concentrations.

TABLE 3

Results for a two-tailed, unequal variance student t-test with 7 degrees of freedom comparing the significance between the results obtained in wired systems and results obtained in wireless systems. The calculated p-value is 0.586, which means we can reject the null hypothesis at a 95% confidence interval.
Two-Tailed, Unequal Variance Student t-Test with 7 Degrees of Freedom

| | Mean | Std. Deviation | t-value | p-value |
|---|---|---|---|---|
| Group 1 - Wired | L0 ppb<br>30 ppb<br>100 ppb<br>250 ppb | 97.5 | 108.743 | 0.570 | 0.586 |

TABLE 3-continued

Results for a two-tailed, unequal variance student t-test with
7 degrees of freedom comparing the significance between the results
obtained in wired systems and results obtained in wireless systems.
The calculated p-value is 0.586, which means we can reject the null
hypothesis at a 95% confidence interval.
Two-Tailed, Unequal Variance Student t-Test with 7 Degrees of Freedom

|  | Mean | Std. Deviation | t-value | p-value |
|---|---|---|---|---|
| Group 2 - Wireless | 0 ppb<br>25 ppb<br>40 ppb<br>60 ppb<br>180 ppb | 61.0 | 70.036 | | |

As explained, the silver electrode often read $Ag^+$ concentrations of about 100 ppb in the control dishes of purified water. In order to determine if the wireless $Ag^+$ concentrations were significant compared to the controls, another independent t-test was performed, with an 85% confidence interval. The t-test performed was two-tailed, with unequal variance. The null hypothesis in this case is that the wireless results are distinguishable from the control. As seen in Table 4, the p-value calculated in 0.119, which is less than 0.15 (for a confidence interval of 85%), therefore confirming that the null hypothesis cannot be rejected, and that the wireless results are indeed distinguishable from the water controls. Furthermore, the t-value calculated is 1.813, which is greater than the given value of 1.65 for a confidence interval of 85%. This means that with 85% confidence, the $Ag^+$ concentrations found in the wireless systems are significantly different than the $Ag^+$ concentrations read by the ISE in the water controls.

TABLE 4

Results for a two-tailed, unequal variance student t-test with
6 degrees of freedom comparing the significance between the results
obtained in the wireless systems to the control measurements in
purified water. The calculated p-value is 0.119, which means we
cannot reject the null hypothesis for an 85% confidence interval.
Two-Tailed, Unequal Variance Student t-Test with 6 Degrees of Freedom

|  | Mean | Std. Deviation | t-value | p-value |
|---|---|---|---|---|
| Group 1 - Water | 100 ppb<br>100 ppb<br>100 ppb<br>100 ppb | 100 | | 1.813 | 0.119 |
| Group 2 - Wireless | 25 ppb<br>50 ppb<br>60 ppb<br>180 ppb | 176.25 | | | |

The wireless system was determined to be a success after multiple readings of significant quantities of silver (>15 ppb silver). The modulated waveform, when passed through a flat copper strip 6 mm over silver washers in a solution of pure water, allowed for a net flow of current on the silver, and thus for silver ions to move off the washer into the solution. The success of the results is based in the fact that while the ion-sensitive electrode often read out very small concentrations of silver in dishes of nothing more than pure water (used as the control), the experiments with the modulated waveform passing over the silver consistently read concentrations of silver higher than those read in the control dishes (Table 2, FIG. 22).

The reason behind the electrode reading silver from solution in which there are no ions is because of the way the electrode works. When placed in a solution, the electrode takes a reading of the voltage difference between the internal reference solution and the external solution in question, and converts that reading to a number of silver particles based on the calibration curve it creates every time the electrode is started up. The electrode is also temperature sensitive, and the proper temperature of solutions being tested should be input to the meter for the calibration curve to be accurate, and it was difficult to ensure that all of the dishes were at the same temperature as the laboratory used had air conditioning vents that allowed for different parts of the room, and thus different trials of the system, to have slightly different temperatures. Even differences as little as one degree Celsius could throw off the electrode, keeping the dishes together helps to keep their temperatures uniform. This resulted in silver concentrations in solutions that clearly had no silver, but as long as the trials actually trying to produce silver read significantly higher concentrations, those trials were considered positive results. Often, the determined concentration would be the difference between the readings in the solution and the reading in the water control; even when silver was read in the control dishes, the readings remaining constant for the duration of that testing period.

Embodiments achieve the goal of providing a wireless electrolysis system for releasing silver ions from plated silver but there are some concerns about the system's use in the human body. In the original setup, using NaCl solution as the electrolyte buffer, the electrode did not read any concentrations of silver, even with the copper conductor and the modulated waveform. The inventors believe that free $A_g+$ and CV ions were combining to form the extremely well-bound AgCl, which can be difficult to separate to release the silver ions that were needed. The solution to this problem was to use pure water to electrolytically isolate the silver.

Silver can be wirelessly produced in a dish with bacteria to observe any inhibition in the bacteria growth due to the silver ions. A blood agar dish is plated with *Staphylococcus aureus* at a concentration of 0.5 McFarland, which is a standard of measurement denoting a density of $10^8$ bacteria cells per milliliter of solution and is often used in similar susceptibility tests. The initial concentration is measured via a comparison of the solution's turbidity to ready-made McFarland standards. Silver discs can be added to the dish, a current can be run through it to produce electrolytically isolated silver, and then the plate can be incubated. An observable zone of inhibited bacteria growth is produced near the silver (where the ions have leeched out) as compared to the outer parts of the agar plate, which will have allowed the *Staphylococcus aureus* to grow uninhibited. This experiment can be repeated multiple times, to see if simulated tissue or anything else interferes with the production of silver ions and if the results are easily replicated. From there, the system can be fine-tuned to account for patients of differing sizes and implants that are covered in a significant amount of connective tissue and muscle. One way to do so would be to reduce the frequency of the waveform, which would increase the skin depth and thus the effectiveness of the wireless system, but may require the system to run for a longer period of time as the change in current (and silver ion production) is reduced.

REFERENCES

The following references are incorporated herein by reference to the maximum extent allowed by law.

Bratzler, D., Houck, P. M., Richards, C., Steele, L., Dellinger, E. P., Fry, D. E., Wright, C., Ma, A. Can, K., Red, L., 2005. Use of antimicrobial prophylaxis for major surgery. Arch Surg. 140, 174.

Benvenisty, A. I., Tannenbaum, G., Ahlborn, T. N., Fox, C. L., Modak, S., Sampath, L., Reemtsma, K., Nowygrod, R., 1988. Control of prosthetic bacterial infection: Evaluation of an easily incorporated, tightly bound, silver antibiotic PTFE graft. J Surg Res. 44, 1.

Cataldo, M. A., Petrosillo, N., Cipriani, M., Cauda, R., Tacconelli, E., 2010. Prosthetic joint infection: recent developments in diagnosis and management. J Infect. 61, 443.

Chen, W. Liu, Y. Courtney, H. S., Bettenga, M., Agrawal, C. M., Bumgardner, J. D., Ong, J. L., 2006. In vitro antibacterial and biological properties of magnetron co-sputtered silver-containing hydroxyapatite coating. Biomaterials. 27, 5512.

Dabasia, H., Kokkinakis, N., El-Guindi, M., 2009. Haematogenous infection of a resurfacing hip replacement after transurethral resection of the prostate. J Bone Joint Surg Br. 91B, 820.

Esposito, S., Leone, S., 2008. Prosthetic joint infections: microbiology, diagnosis, management, and prevention. Int J Antimicrob Agents. 32, 287.

Gao, H., Sandermann, J., Prag, J., Lund, L., Lindholt, J. S., 2010. Prevention of primary vascular graft infection with silver coated polyester graft in a porcine model. Europen J of Vascular and Endovascular Surgery. 39, 472.

Gollwitzer, H., Ibrahim, K., Meyer, H., Mittelmeier, W., Busch, R., Stemberger, A., 2003. Antibacterial poly(D,L-lactic acid) coating of medical implants using a biodegradable drug delivery technology. J Antimicrobial Chemotherapy. 51, 585.

Hetrick, E. M., Schoenfisch, M. H., 2006. Reducing implant-related infections: active release strategies. Chem Soc Rev. 35, 780.

Kendoff, D. and Gehrke, T., 2012. Focus on one stage exchange arthroplasty: the devil is in the detail. J Bone Joint Surg.

MacDonald, S. J., McCalden, R. W., Chess, D. G., Bourne, R. B., Rorabeck, C. H., Cleland, D., Leung, F., 2003. Metal-on-metal versus polyethylene in hip arthroplasties: a randomized clinical trial. Clin Orthop Relat Res. 406, 282.

Madu, K. A. et al. 2011. Implant associated surgical site infection in orthopedics: a regional hospital experience. J of Med. 20, 435.

Morones-Ramirez, J. R., Winkler, J. A., Spina, C. S., Collins, J. J., 2013. Silver enhances antibiotic activity against gram-negative bacteria. Sci Trans Med. 5, 1.

Percival, S. L., Thomas, J., Linton, S., Okel, T., Corum, L., Slone, W., 2012. The antimicrobial efficacy of silver on antibiotic resistant bacteria isolated from burn wounds. Int Wound Journal. 9, 488.

Richards, R. G., Persson, A., Gasser, B., Wielding, R., 2002. Influence of surface microtopography on formation of capsules, an in vivo study of stainless steel implants in rabbits. J Bone Joint Surg. 84B.

Secinti, K. D., Ayten, M., Kahilogullari, G., Kaygusuz, G., Ugar, H. C., Attar, A., 2008. Antibacterial effects of electrically activated vertebral implants. J Clin Neuro. 15, 434.

Stigter, M., Bezemer, J., Groot, K., Layrolle, P., 2004. Incorporation of different antibiotics into carbonated hydroxyapatite coatings on titanium implants, release and antibiotic efficacy. J Controlled Release. 99, 127.

Szabo, T., et al., 1977. Periodic Surface Acoustic Wave Electromagnetic Transducers. *IEEE Transactions on Sonics and Ultrasonics* 24, 393.

Trebse, R., Pisot, V., Trampuz, A., 2005. Treatment of infected retained implants. J Bone Joint Surg. 87B, 249.

Widmer, A. F., 2001. New developments in diagnostics and treatment of infection in orthopedic implants. Clin Inf Dis. 33, 94.

Zhao, L., Chu, P. K., Zhang, Y., Wu, Z., 2009. Antibacterial coatings on titanium implants. J Biomed Mater Res. 91B, 470.

Experiments

| Date | Exp. # | Direct or Wireless | Current/Waveform/Voltage | Solution Medium | Conductor | Time Period | Results [silver] in ppb |
|---|---|---|---|---|---|---|---|
| Sept. 23 | 1 | Direct | 2 MHz Sine Wave | NaCl | — | 5 Hours | 0 |
| Sept. 23 | 2 | Wireless | 8 MHz Sine Wave | NaCl | Multi-Conductor | 5 Hours | 0 |
| Oct. 7 | 3 | Wireless | 100 Hz Sine Wave | NaCl | Multi-Conductor | 5 Hours | 0 |
| Oct. 7 | 4 | Wireless | Modulated Waveform | NaCl | Multi-Conductor | 5 Hours | 0 |
| Oct. 22 | 5 | Direct | 20 μA | NaCl | — | 12 Hours | 0 |
| Oct. 22 | 6 | Direct | 20 μA | NaCl | — | 12 Hours | 0 |
| Oct. 25 | 7 | Direct | 20 μA | NaCl | — | 22 Hours | 0 |
| Oct. 25 | 8 | Direct | 20 μA | NaCl | — | 22 Hours | 0 |
| Oct. 26 | 9 | Direct | 60 μA | Tap Water | — | 40 Hours | 0.4 |
| Oct. 26 | 10 | Direct | 20 μA | NaCl | — | 40 Hours | 0 |
| Oct. 28 | 11 | Wireless | Modulated Waveform | NaCl | Copper Strip | 5 Hours | 0 |
| Oct. 28 | 12 | Direct | 12 mA | NaCl | — | 2 Hours | 0 |
| Nov. 16 | 13 | Direct | 20 V | Purified Water | — | 20 Min | 1000 |
| Nov. 16 | 14 | Direct | 200 mA | Purified Water | — | 20 Min | 700 |
| Nov. 16 | 15 | Wireless | Modulated Waveform | Purified Water | Copper Strip | 5 Hours | 0 |
| Nov. 18 | 16 | Direct | 20 μA | Purified Water | — | 4 Hours | 10 |

-continued

| Date | Exp. # | Direct or Wireless | Current/ Waveform/ Voltage | Solution Medium | Conductor | Time Period | Results [silver] in ppb |
|---|---|---|---|---|---|---|---|
| Nov. 18 | 17 | Direct | 1 mA | Purified Water | — | 4 Hours | 15 |
| Nov. 20 | 18 | Wireless, Diode Bridge | 100 Hz Sine Wave | Purified Water | Copper Strip | 4 Hours | 0 |
| Nov. 20 | 19 | Direct, Diode Bridge | 10 kHz Sine Wave | Purified Water | — | 4 Hours | 0 |
| Nov. 20 | 20 | Direct | 1 mA | Purified Water | — | 4 Hours | 15 |
| Nov. 20 | 21 | Direct | 240 mA | Purified Water | — | 4 Hours | 53 |
| Nov. 22 | 22 | Wireless | Modulated Waveform | Purified Water | Copper Strip | 6 Hours | 0 |
| Nov. 22 | 23 | Direct, Diode Bridge | 100 Hz Sine Wave | Purified Water | — | 6 Hours | 0 |
| Nov. 22 | 24 | Wireless, Diode Bridge | 100 Hz Sine Wave | Purified Water | Copper Strip | 6 Hours | 0 |
| Nov. 22 | 25 | Direct | 20 μA | Purified Water | — | 6 Hours | 30 |
| Nov. 23 | 26 | Wireless | Modulated Waveform | Purified Water | Copper Strip | 12 Hours | 40 |
| Nov. 23 | 27 | Wireless | Modulated Waveform | Purified Water | Copper Strip | 12 Hours | 25 |
| Nov. 23 | 28 | Wireless | Modulated Waveform | Purified Water | Copper Strip | 12 Hours | 40 |
| Nov. 23 | 29 | Wireless | 100 Hz Sine Wave | Purified Water | Copper Strip | 12 Hours | 100 |
| Nov. 23 | 30 | Direct | 20 μA | Purified Water | — | 12 Hours | 250 |
| Nov. 23 | 31 | Direct | 20 μA | Purified Water | — | 12 Hours | 100 |
| Nov. 26 | 32 | Wireless | Modulated Waveform | Purified Water | Copper Strip | 14 Hours | 60 |
| Nov. 26 | 34 | Wireless | 100 Hz Sine Wave | Purified Water | Copper Strip | 14 Hours | 30 |
| Dec. 3 | 35 | Wireless | 100 Hz Sine Wave | Purified Water | Copper Strip | 20 Hours | 200 |
| Dec. 3 | 36 | Wireless | Modulated Waveform | Purified Water | Copper Strip | 20 Hours | 180 |

1. Quasi-Rectification of Wirelessly-induced Eddy Currents for Inverse (and Direct) Electrolysis of Ag⁺ Ions The present section explains the theoretical mechanism of quasi-rectification for inverse (and direct) electrolysis of Ag+ ions.

1.1 Simplified Treatment of Tissue Eddy Current Density Excited by an External Radiator The accurate modeling of the present problem should include a transient analysis of the eddy-current distribution in a realistic femur phantom—see FIG. 22—with an implant, via the Finite Element Method (FEM) or the Boundary Element Method (BEM) [1]. The model given below is an approximation, which is frequently employed for useful estimations [2-4].

Namely, for a homogeneous conducting medium where the temporal diffusion of eddy currents has a relatively small effect when compared to their direct excitation (the skin layer depth is very large), the expression for the eddy current density J(r,t) in terms of the coil current i(t) is given by the integral $$J(r, t) = -\frac{\mu_0 \sigma}{4\pi} \frac{di(t)}{dt} \oint_L \frac{dl}{|r - r'(l)|} \quad (1)$$

Here, $\mu_0$ is the magnetic permeability of free space, $\sigma$ is the (average) conductivity, and r'(l) belongs to the coil contour, L. Eq. (1) in particular demonstrates that a true rectification of eddy currents without external means is impossible since the wireless link is indeed a linear system. However, a quasi-rectification is possible as explained below.

1.2 Quasi-rectification of Modulated Carrier Pulses

Consider the exciting current in the form of an exponentially decaying carrier, as shown in FIG. 23A $$i(t) = I_0 \exp\left(-\frac{t}{\tau}\right) \cos \omega t \quad (2)$$

which repeats itself multiple times. Here, $\omega$ and $\tau$ are signal parameters to be optimized for maximum performance. Eq. (2) is substituted into Eq. (1) and the eddy current density is evaluated. FIG. 23B shows a generic eddy current density in tissue for $\omega$=50 rad/s, $\tau$=1 s. The averaged value of the current density over the carrier period, $\overline{J(r,t)}$, is plotted.

An important point in FIG. 23B is the presence of a relatively long phase of negative direct current, which stimulates inverse electrolysis (i.e., the release) of Ag⁺ ions over a greater time interval. At the same time, an intense but very short phase of the positive direct current has a much smaller relative effect on the inverse electrolysis, supposedly, due to non-equivalent mechanical motion. This is confirmed experimentally. Switching the exciting current polarity will reverse the phases.

REFERENCES

The following references are incorporated herein by reference to the maximum extent allowed by law.

[1] Kriezis E E, Tsiboukis T D, Panas S M, Tegopoulos J A, eddy currents: theory and applications, *IEEE Proceedings,* 1992; 80:1559-89.
[2] Grandori F, Ravazzani P, Magnetic stimulation of the motor cortex. Theoretical considerations, *IEEE Trans. Biomed. Engineering,* 1991; 38:180-91.
[3] Li Y, Tian G Y, Simm A, Fast analytical modelling for pulsed eddy current evaluation, *NDT&E International,* 2008; 41:477-483.
[4] Noetscher G M, Makarov S N, Sciré-Scappuzzo F, Pascual-Leone A, A simple absolute estimate of peak eddy currents induced by TMS using the GR model, IEEE Trans. Magnetics, 2013; 49: 4999-5003.

GLOSSARY

Arthroplasty The surgical repair of a joint
$Ag^+$ Positively charged silver ions
Anodization To coat a metal surface electrolytically with oxide
Bactericidal Destructive to bacteria
Biofilm Group of microorganisms in which cells stick to each other and to a surface
Colloidal Silver Contains silver particles suspended in fluid
Debridement The removal of dead, damaged, or infected tissue
Electrolysis The use of a direct current to drive a non-spontaneous reaction
Hydroxyapatite Naturally occurring mineral form of calcium apatite
Induction The production of voltage across a conductor when it is exposed to a varying magnetic field
ISE Ion sensitive electrode
Microbicidal Destructive to microbes
NaCl Sodium chloride
Perioperative Time period describing the duration of a patient's surgical procedure
Prophylaxis Action taken to prevent disease

Having thus described at least one illustrative embodiment of the invention, various alterations, modifications, and improvements will readily occur to those skilled in the art. Such alterations, modifications, and improvements are intended to be part of this disclosure, and are intended to be within the spirit and scope of the present invention. Accordingly, the foregoing description is by way of example only and is not intended to be limiting. The present invention is limited only as defined in the following claims and the equivalents thereto.

The invention claimed is:

1. A device for releasing agents from a medical implant in an organism, the device comprising:
a power supply configured to produce a time-varying voltage; and
a conducting material configured to:
receive the time-varying voltage across the conducting material, forming a time-varying current through the conducting material;
transmit a time-varying magnetic field in response to the time-varying current; and
position at a distance from the medical implant, wherein the medical implant receives the time-varying magnetic field and releases the agents based on an induced current in response to the time-varying magnetic field, wherein the distance of the conducting material positioned to the medical implant is based on a frequency parameter of the time-varying voltage.

2. The device of claim 1, the device further comprising:
a mechanism for securing the conducting material to a surface of the organism in proximity to the medical implant, wherein the conducting material conforms to the surface of the organism.

3. The device of claim 1, the device further comprising:
a switch configured to control a connection between the power supply and the conducting material, wherein the switch has a connected state where the power supply and the conducting material are connected and a disconnected state where the power supply and the conducting material are disconnected.

4. The device of claim 1, wherein the agents have antimicrobial properties.

5. The device of claim 1, wherein the agents are silver ions.

6. The device of claim 1, wherein the time-varying voltage has a net positive voltage or a net negative voltage.

7. The device of claim 1, wherein the induced current is produced by a wireless mode.

8. The device of claim 7, wherein the wireless mode is electromagnetic induction.

9. The device of claim 1, wherein the time-varying magnetic field is a wireless signal transmitted by the conducting material and received by the medical implant.

10. The device of claim 9, wherein the agents are activated by the wireless signal.

11. An apparatus comprising:
a first conducting material configured to receive a time-varying current based on an applied time-varying voltage across the first conducting material;
a second conducting material positioned a distance from the first conducting material, wherein a portion of the second conducting material contacts a solution and the second conducting material has an electron flow in the presence of the time-varying current through the first conducting material; and
a plurality of agents on the second conducting material, wherein the plurality of agents are configured to release into the solution from the second conducting material in the presence of the electron flow, and wherein at least a portion of the plurality of agents, after being released into the solution, return to the second conducting material based on changing at least one parameter of the time-varying voltage.

12. The apparatus of claim 11, the apparatus further comprising:
a switch configured to control the time-varying current in the first conducting material, wherein the switch has:
a disconnected state that stops current through the first conducting material; and
a connected state that allows current through the first conducting material.

13. The apparatus of claim 11, wherein the applied time-varying voltage has a net positive voltage or a net negative voltage.

14. The apparatus of claim 11, wherein the distance of the first conducting material positioned to the second conducing material is based on a frequency parameter of the applied time-varying voltage.

15. The apparatus of claim 11, wherein the plurality of agents are further configured to be immobilized on the second conducting material before the electron flow occurs.

16. The apparatus of claim 11, wherein the second conducting material is a medical implant.

17. The apparatus of claim 11, wherein the plurality of agents have antimicrobial properties.

18. The apparatus of claim 11, wherein the plurality of agents are silver ions.

19. The apparatus of claim 11, wherein the electron flow in the second conducting material is produced by a wireless mode.

20. The apparatus of claim 19, wherein the wireless mode is electromagnetic induction.

21. The apparatus of claim 11, wherein the electron flow in the second conducting material is produced by the first conducting material transmitting a wireless signal and the second conducting material receiving the wireless signal.

22. The apparatus of claim 21, wherein at least a portion of the plurality of agents are activated by the wireless signal.

23. A system comprising:
a power source supplying a voltage signal;
a waveform generator configured to produce a time-varying voltage from the voltage signal based on at least one parameter;
a transmitting electrode configured to receive the time-varying voltage across the transmitting electrode from the waveform generator, wherein:
a time-varying current through the transmitting electrode forms based on the time-varying voltage; and
the transmitting electrode transmits a time-varying magnetic field based on the time-varying current;
a receiving electrode positioned to receive the time-varying magnetic field, inducing an electron flow in the receiving electrode based on the time-varying magnetic field; and
a plurality of agents released from the receiving electrode in the presence of the electron flow in the receiving electrode, and wherein at least a portion of the plurality of agents, after being released, return to the receiving electrode based on changing at least one parameter of the time-varying voltage.

24. The system of claim 23, the system further comprising:
a switch configured to control the time-varying current through the transmitting electrode, wherein the switch has a disconnected state disconnecting the transmitting electrode from receiving the time-varying current and a connected state connecting the transmitting electrode to receive the time-varying current.

25. The system of claim 23, wherein the plurality of agents are immobilized on the receiving electrode prior to positioning it to receive the time-varying magnetic field.

26. The system of claim 23, wherein the plurality of agents have antimicrobial properties.

27. The system of claim 23, wherein the plurality of agents are silver ions.

28. The system of claim 23, wherein the electron flow in the receiving electrode is produced by a wireless mode.

29. The system of claim 28, wherein the wireless mode is electromagnetic induction.

30. The system of claim 23, wherein the electron flow in the receiving electrode is produced by the transmitting electrode transmitting a wireless signal and the receiving electrode receiving the wireless signal.

31. The system of claim 30, wherein at least a portion of the plurality of agents are activated by the wireless signal.

32. An apparatus comprising:
a first conducting material configured to receive a time-varying current based on an applied time-varying voltage across the first conducting material;
a second conducting material positioned a distance from the first conducting material, wherein the distance of the first conducting material positioned to the second conducing material is based on a frequency parameter of the applied time-varying voltage, and wherein a portion of the second conducting material contacts a solution and the second conducting material has an electron flow in the presence of the time-varying current through the first conducting material; and
a plurality of agents on the second conducting material, wherein the plurality of agents are configured to release into the solution from the second conducting material in the presence of the electron flow.

33. The apparatus of claim 32, wherein at least a portion of the plurality of agents, after being released into the solution, return to the second conducting material based on changing at least one parameter of the time-varying voltage.

34. The apparatus of claim 32, wherein the plurality of agents are further configured to be immobilized on the second conducting material before the electron flow occurs, and wherein the second conducting material is a medical implant.

35. The apparatus of claim 32, wherein the electron flow in the second conducting material is produced by the first conducting material transmitting a wireless signal and the second conducting material receiving the wireless signal, wherein at least a portion of the plurality of agents are activated by the wireless signal, and wherein the plurality of agents have antimicrobial properties.

\* \* \* \* \*